United States Patent
Moberg

(10) Patent No.: US 11,464,706 B2
(45) Date of Patent: Oct. 11, 2022

(54) AUTOMATED DRUG DELIVERY DEVICE AND CONTAINER

(71) Applicant: AMGEN INC., Thousand Oaks, CA (US)

(72) Inventor: Sheldon B. Moberg, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 0 days.

(21) Appl. No.: 17/435,421

(22) PCT Filed: Apr. 1, 2020

(86) PCT No.: PCT/US2020/026071
§ 371 (c)(1),
(2) Date: Sep. 1, 2021

(87) PCT Pub. No.: WO2020/210094
PCT Pub. Date: Oct. 15, 2020

(65) Prior Publication Data
US 2022/0096326 A1 Mar. 31, 2022

Related U.S. Application Data

(60) Provisional application No. 62/830,887, filed on Apr. 8, 2019.

(51) Int. Cl.
*A61J 1/16* (2006.01)
(52) U.S. Cl.
CPC .......... *A61J 1/16* (2013.01); *A61J 1/165* (2013.01); *A61J 2200/42* (2013.01); *A61J 2200/72* (2013.01)
(58) Field of Classification Search
CPC ...... G07F 11/62; G07F 9/105; G07F 17/0078; A61J 1/165

(Continued)

(56) References Cited

U.S. PATENT DOCUMENTS

| | | | | |
|---|---|---|---|---|
| 6,125,082 A | * | 9/2000 | Reid | A24F 15/005 368/10 |
| 7,861,538 B2 | * | 1/2011 | Welle | F25B 21/04 62/3.62 |

(Continued)

FOREIGN PATENT DOCUMENTS

| WO | WO-2017106247 A1 * | 6/2017 | .......... A61J 7/0409 |
|---|---|---|---|
| WO | WO-2018202677 A1 | 11/2018 | |

OTHER PUBLICATIONS

International Search Report for International Application No. PCT/US2020/026071, dated Jun. 17, 2020.

(Continued)

*Primary Examiner* — Timothy R Waggoner
(74) *Attorney, Agent, or Firm* — Marshall, Gerstein & Borun LLP

(57) ABSTRACT

A drug delivery system includes a drug delivery device that delivers medicament to a user and a storage container having a container body that defines at least one storage compartment. The storage container includes a controller, at least one temperature sensor associated with the at least one storage compartment, at least one temperature control device associated with the at least one storage compartment, and at least one retention mechanism coupled to the storage container. In response to a user input, the controller is adapted to activate the at least one temperature control device to adjust the temperature in the at least one storage compartment to an administration temperature and transmit a signal to the at least one retention mechanism to release the drug delivery device from the at least one storage compartment after the temperature in the at least one storage compartment reaches the administration temperature.

18 Claims, 3 Drawing Sheets

(58) Field of Classification Search
USPC .................................................. 221/192, 191
See application file for complete search history.

(56) References Cited

U.S. PATENT DOCUMENTS

| | | | | |
|---|---|---|---|---|
| 11,207,460 | B2* | 12/2021 | Tamtoro | A61M 5/002 |
| 2009/0100843 | A1* | 4/2009 | Wilkinson | F25B 21/02 |
| | | | | 62/3.7 |
| 2010/0282762 | A1* | 11/2010 | Leonard | B65D 81/3841 |
| | | | | 220/592.01 |
| 2014/0158703 | A1* | 6/2014 | Niinisto | A61J 7/0409 |
| | | | | 221/1 |
| 2018/0193552 | A1 | 7/2018 | Wright et al. | |
| 2020/0224964 | A1* | 7/2020 | Alexander | F25B 21/04 |

OTHER PUBLICATIONS

Written Opinion of the International Searching Authority for International Application No. PCT/US2020/026071, dated Jun. 17, 2020.

* cited by examiner

AUTOMATED DRUG DELIVERY DEVICE AND CONTAINER

CROSS-REFERENCE TO RELATED APPLICATIONS

This is the United States National Phase of PCT/US20/26071, filed Apr. 1, 2020, which claims priority to U.S. Provisional Patent Application No. 62/830,887, filed Apr. 8, 2019, the entire contents of each of which are hereby expressly incorporated herein by reference.

FIELD OF DISCLOSURE

The present disclosure generally relates to drug delivery devices and methods. More particularly, the present disclosure relates to improved containers having heating and cooling features for housing drug delivery devices.

BACKGROUND

Drugs are administered to treat a variety of conditions and diseases. Autoinjectors and on-body injectors (e.g., pen style autoinjectors) offer several benefits in delivery of medicaments and/or therapeutics. One of the benefits can include simplicity of use, as compared with traditional methods of delivery using, for example, conventional syringes. Autoinjectors may be used to deliver a number of different drugs having varying viscosities and/or desired volumes.

Many medicaments require refrigeration to maintain stability and performance. Accordingly, it is common for these medicaments to be labeled for cold storage during manufacturing, transportation, and storage processes prior to patient and/or clinician use. These medicaments are often stored at temperatures ranging from approximately 2° C. and approximately 8° C. to support standard household refrigerators, and must be sufficiently warmed prior to administration in order to minimize pain and to ensure the delivery device functions properly and as intended. Patients may be hesitant to administer these drugs due to warming techniques which may result in risking administering a cold injection or require extended delivery times if the patient fails to wait an appropriate length of time after removing the device from refrigeration. These contributing factors which may extend the time of the perceived injection experience or add discomfort to the user may risk reducing adherence to therapy.

Patients desire both a comfortable and predictable injection experience. Administering injections using devices at substantially similar temperatures often yields substantially similar experiences. Differences of medicament temperatures at the time of administration of approximately 5° C. or more are likely to cause discernible differences to the patient, particularly in medicaments having highly temperature-dependent viscosities, which may lead to hesitation and uncertainty in administering subsequent doses. This in turn may lead to reduced adherence levels.

However, some household refrigerators are unable to maintain stable temperatures within this range, and as a result, drug products and/or delivery devices stored in these units may become damaged. Additionally, users may forget to administer the medicament after warming the product to a use temperature, and as such, the medicament may be inadvertently left at this temperature for a prolonged period of time that causes the medicament to spoil or otherwise be damaged. Further, in some use environments, the medicine may be removed from the packaging in order to reduce space in the refrigerator, and thus may expose the medicinal product, which may be unsafe and/or result in privacy concerns. Last, there may be a risk of non-prescribed patients using these devices, and patients may be uncertain as to whether they have used a device in question.

As described in more detail below, the present disclosure sets forth automated drug delivery devices and storage containers embodying advantageous alternatives to existing systems and methods, and that may address one or more of the challenges or needs mentioned herein, as well as provide other benefits and advantages.

SUMMARY

In accordance with a first aspect, a drug delivery system includes a drug delivery device that delivers medicament to a user and a storage container having a container body that defines at least one storage compartment. The storage container includes a controller, at least one temperature sensor associated with the at least one storage compartment, at least one temperature control device associated with the at least one storage compartment, and at least one retention mechanism coupled to the storage container. In response to a user input, the controller is adapted to activate the at least one temperature control device to adjust the temperature in the at least one storage compartment to an administration temperature and transmit a signal to the at least one retention mechanism to release the drug delivery device from the at least one storage compartment after the temperature in the at least one storage compartment reaches the administration temperature.

In some examples, the controller may further transmit a signal to the at least one retention mechanism to re-secure the drug delivery device within the at least one storage compartment after a predetermined time elapses, which may be approximately 30 minutes. The at least one temperature control device may include at least one of a cooling element or a heating element, and the at least one temperature controller may adjust the temperature between a cooling temperature and the administration temperature. The cooling temperature may be between approximately 0° C. and approximately 10° C. The administration temperature may between approximately 20° C. and approximately 40° C.

In some forms, the release mechanism may be in the form of a locking member that provides access to the at least one storage compartment. In some examples, a plurality of storage compartments may be provided, each of which can contain a drug delivery device therein. Each of these storage compartments may include a respective retention mechanism that selectively retains the drug delivery device therein. Further, the system may include a number of temperature control devices, each of which is associated with one of the plurality of storage compartments.

The at least one retention mechanism may be in the form of a movable platform that selectively raises or lowers the drug delivery device. The system may further include an interface that receives the user input. The interface may include at least one of a desired drug delivery time, a dosage quantity, or a temperature set point.

In accordance with a second aspect, an automated storage container for storing a drug delivery device includes at least one storage compartment, a controller operably coupled to the storage container and being adapted to control operation thereof, at least one temperature sensor associated with the at least one storage compartment, at least one temperature control device associated with the at least one storage compartment, and at least one retention mechanism coupled to the storage container. The temperature sensor is communicatively coupled to the controller to measure a temperature of the at least one storage compartment and to transmit the measured temperature to the controller. The temperature control device is communicatively coupled to the controller to adjust a temperature of the at least one storage compartment. The retention mechanism is communicatively coupled to the controller to selectively retain the drug delivery device within the at least one storage compartment. In response to a user input, the controller activates the at least one temperature control device to adjust the temperature in the at least one storage compartment to an administration temperature. The controller further transmits a signal to the at least one retention mechanism to release the drug delivery device from the at least one storage compartment after the temperature in the at least one storage compartment reaches the administration temperature.

BRIEF DESCRIPTION OF THE DRAWINGS

The above needs are at least partially met through provision of the automated drug delivery device and container described in the following detailed description, particularly when studied in conjunction with the drawings, wherein.

Figure 1:
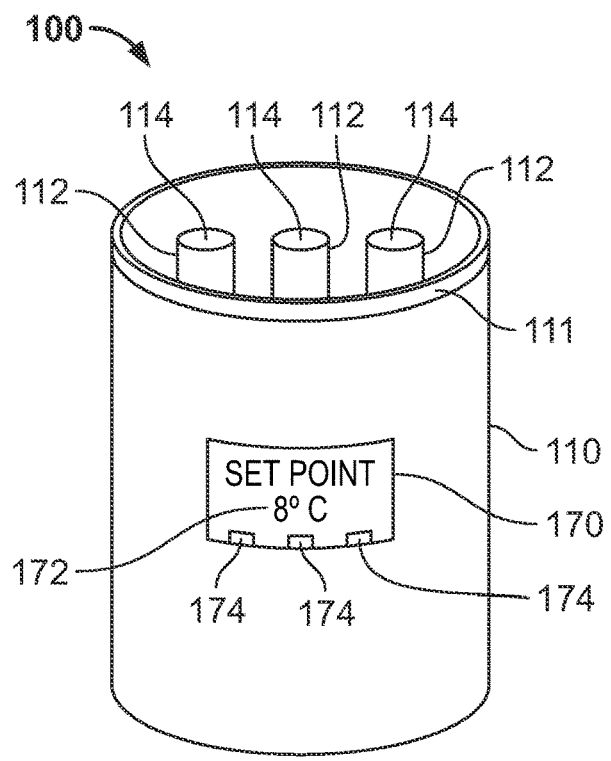
FIG. 1 illustrates a perspective view of an example drug delivery system in a first orientation in accordance with various embodiments.
Figure 2:
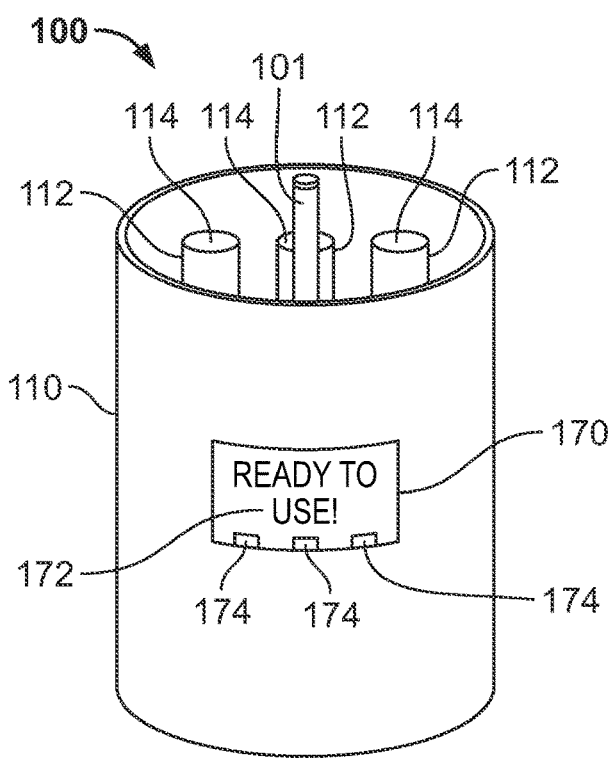
FIG. 2 illustrates a perspective view of the example drug delivery system of FIG. 1 in a second orientation in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a tabletop drug delivery system includes a drug delivery device (e.g., an autoinjector or other injector, a Pre-Filled Syringe ("PFS"), a vial, or other drug storage mechanism) selectively retained within a storage container having one or more storage compartments therein. Such a system may mitigate many of the issues associated with storing the drug product in a refrigerator by providing a convenient, automated system having robust functionality. For example, the system may include both cooling and heating systems that allow the drug delivery device to be stored at an ideal storage temperature that 1) prolongs the life of the drug contained within the device; and 2) allows the drug and the drug delivery device to be warmed to a comfortable administration temperature that ensures patient comfort. Such a system may be used at a patient's home or at a healthcare facility that stores, administers, and/or provides dosages to patients.

The drug delivery device may be in the form of an autoinjector, PFS, or an on-body injector or infuser (the reference to injector intended to include also a reference to an infuser, to the extent that a difference is suggested), a vial, or other drug storage mechanism. Autoinjectors may be single-use devices which administer a single dose during a single application of the device to the users skin, although autoinjectors are not limited to only single-use devices—they may be multi-use devices as well. On-body injectors may be multi-use devices, administering multiple doses during one or more applications of the device to the users skin, although on-body devices may also be used as single-use devices. Either autoinjectors or on-body injectors may have assemblies or sub-assemblies that are reusable, in that the assemblies may be used and re-used by refilling the reservoir, by removing an empty reservoir and replacing it with a filled reservoir, or by replacing the cannula, for example.

As illustrated in the Figures, an example drug delivery system 100 is provided which includes a drug delivery device 101, a storage container 110 including at least one storage compartment 112 disposed within the storage container 110, a controller 120 having a processor, memory, and computer-executable instructions and/or logic, at least one temperature sensor 130, at least one temperature control device 140, and at least one retention mechanism 150. The system 100 may further include a sealing device such as a lid 111, a communication device (not shown), and any number of additional sensors, components, and or other arrangements.

The storage container 110 may be constructed of any number of materials ranging from paper-based materials, polymers or other plastics, metals, and/or any combination of the same. The storage container 110 may be any shape (e.g., cylindrical) and defines a cavity or cavities for each of the storage compartments 112, or may be a solid, non-hollow configuration, or may have any combination of hollow and solid portions. The storage container 110 may include any type of power source such as a rechargeable power station or an onboard battery to provide power to the system 100. Such a system may provide protection against power outages and maintain desired set temperatures and other functionality for the duration of the battery charge, and may be arranged to last approximately 24 hours or more.

The storage container 110 may accommodate any number of storage compartments 112 which may be configured in a number of ways such as a number of elongated capsules (as illustrated in the Figures), a recessed area disposed on a surface of the storage container 110, a drawer-based system, a sealed package, box, and/or pouch, and the like. The storage compartments 112 may be dimensioned to accommodate the drug delivery device 101 in an inner volume thereof, and facilitate rapid and non-degrading temperature adjustment of the drug delivery device 101 disposed therein.

The storage compartment 112 may include any number of devices such as screens, vents, and the like to manage airflow to a cavity therein. Other examples are possible.

The storage compartment 112 includes a compartment lid 114 that closes and/or seals the storage compartment 112. In the illustrated example, the compartment lid 114 is in the form of hinged doors that open when pushed from the inside of the storage compartment 112. The lid 111 may similarly be configured in a number of ways, for example, a hinged flap or door and/or a removable portion may be utilized. In some examples (e.g., where the storage container 110 includes a single storage compartment 112), the lid 111 assists in sealing the storage compartment 112. The storage compartment 112 further includes a retention mechanism 150 which, as will be discussed in further detail, selectively retains and releases the drug delivery device 101 within the storage compartment 112.

Figure 3:
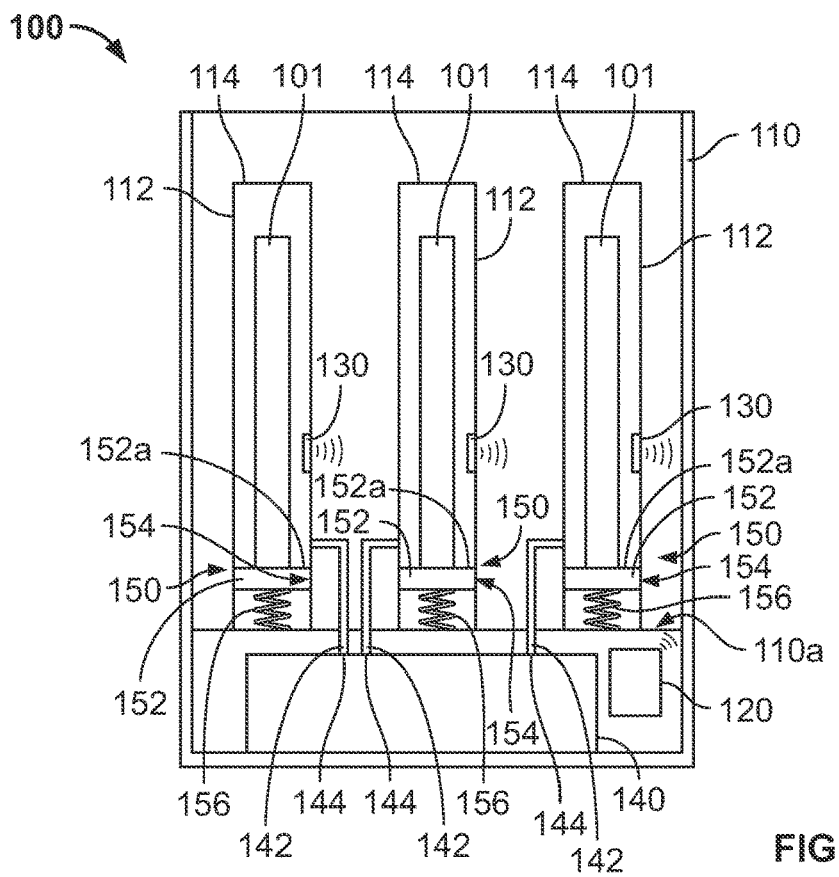
FIG. 3 illustrates a front cross-sectional elevation view of the example system of FIGS. 1 and 2 in the first orientation in accordance with various embodiments.
Figure 4:
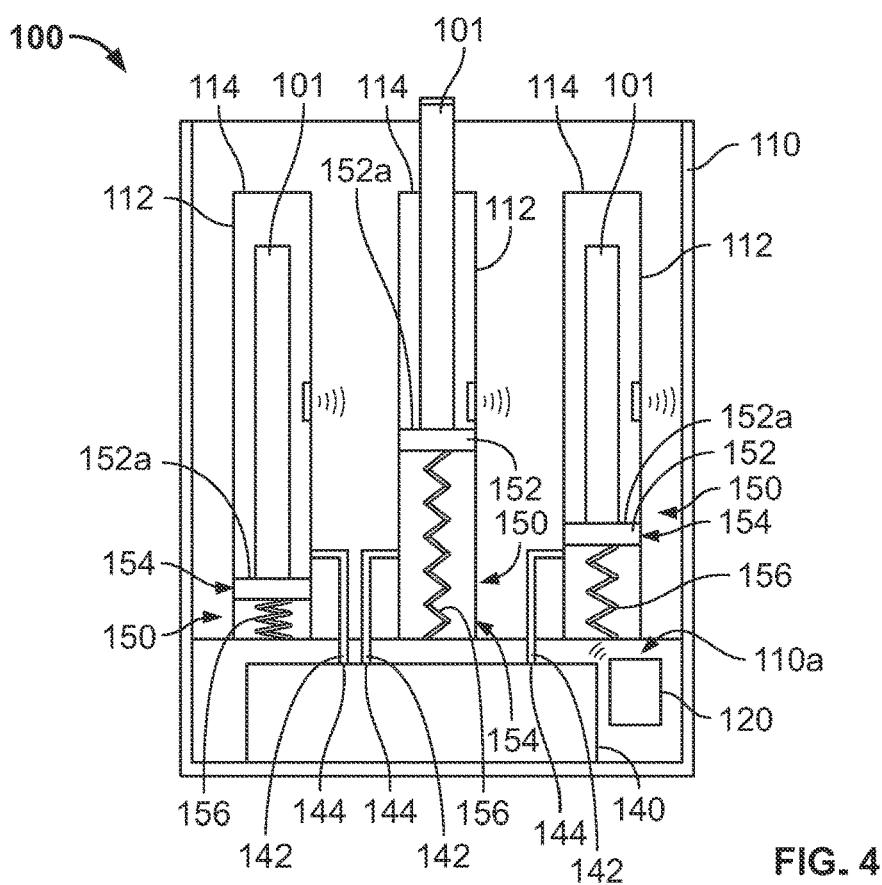
FIG. 4 illustrates a front cross-sectional elevation view of the example system of FIGS. 1-3 in the second orientation in accordance with various embodiments.

As previously noted, the controller 120 may include any number of components such as a processor, memory, and computer-executable instructions and/or logic used to control operation of the system 100. As illustrated in FIGS. 3 and 4, the controller 120 may be disposed within a lower cavity 110a of the storage container 110 that may be inaccessible to the patient or user. The controller 120 may include any number of signal transmitters and/or receivers to transmit or receive data from components in the system 100. The controller 120 is adapted to communicate via any number of communication protocols, for example wired (e.g., via serial, USB, CAT-5, CAT-6, and the like), wireless (e.g., via Wi-Fi, RFID, NFC, Zigbee, Bluetooth, and the like).

The at least one temperature sensor 130 may be any type of sensor adapted to sense a temperature within the storage compartment 112, and may be disposed in any number of locations relative to the storage compartment 112, such as, for example, within a volume of the storage compartment 112, disposed through or on a sidewall of the storage compartment 112, and the like. Other examples are possible. Any number of temperature sensors 130 may be used that correspond to the number of storage compartments 112 disposed within the storage container 110. The temperature sensor 130 may be an active and/or a passive sensor such as infrared sensors, switches, circuits, and the like. In some approaches. The temperature sensor 130 may communicate with the controller 120 via any number of the previously-described communication protocols.

The temperature control device 140 is associated with each of the storage compartments 112 and is communicatively coupled to the controller 120 via any number of the previously-described communication protocols. The temperature control device 140 may be disposed in the lower cavity 110a of the storage container 110. In some examples, the temperature control device 140 may selectively heat and/or cool the storage compartments 112 disposed within the storage container 110. For example, the temperature control device 140 may adjust a temperature within the storage compartments 112 from a cooling temperature (e.g., between approximately 0° C. and approximately 10° C., preferably between approximately 2° C. and approximately 8° C.) to an administration temperature (e.g., between approximately 15° C. and approximately 35° C., and preferably between approximately 22° C. and approximately 28° C.).

The temperature control device 140 may be in the form of a heat pump refrigerant system, a Peltier device, or any other thermoelectric cooler. Some systems such as Peltier-based systems may provide an additional advantage as being silent, small, simple, and can readily support heating or cooling in small controlled spaces.

In the illustrated example, a single temperature control device 140 is coupled to each of the storage compartments 112 via a connection member 142 that functions as ventilation that selectively transmits warmed or cooled fluid (e.g., air) into the storage compartment or compartments 112. Such a system may incorporate any suitable valve mechanism 144 that selectively restricts fluid flow depending on the desired heating or cooling effect to be achieved. In other arrangements, each storage compartment 112 may have separate connection members 142 for providing hot or cold fluid. When hot fluid is desired, a valve mechanism 144 associated with the cold fluid connection member may restrict cold fluid from flowing to the storage compartment 112, and when cold fluid is desired, a valve mechanism 144 associated with the hot fluid connection member may restrict hot fluid from flowing to the storage compartment 112. In other examples, a first temperature control device 140 may be used solely for the purpose of providing cooling to the storage compartments 112, and a separate temperature control device 140 may be used solely for the purpose of providing heating to the storage compartments 112. In these examples, selective valve mechanisms 144 may be actuated to selectively permit or restrict fluid from flowing into respective connection members 142 to heat or cool the storage compartments 112. In yet other examples, any number of temperature control devices 140 may be used that correspond to the number of storage compartments 112 disposed within the storage container 110. Other arrangements are possible.

As illustrated in FIGS. 3 and 4, the retention mechanism 150 is coupled to the storage container 110 and is communicatively coupled to the controller 120 to selectively retain the drug delivery device 101 within its respective storage compartment 112. In the illustrated example, the retention mechanism 150 is in the form of a platform 152, a locking member 154, and a drive member 156. The platform 152 includes an upper surface 152a and is movable between a first, lowered position and a second, raised position. In some examples, movement of the platform 152 may be guided by the inner diameter of the storage compartment 112, or in other examples, a track or other guiding mechanism (not shown) may be provided. The drug delivery device 101 rests on and/or is retained by the upper surface 152a of the platform 152, which may have a recession formed thereon that is shaped to correspond to the shape of the drug delivery device 101. In such an example, the drug delivery device 101 may be inserted into this recession to stabilize the device 101 within the storage compartment 112.

The locking member 154 may be in the form of a movable latch that selectively engages a portion of the platform 152 such as a notch or detent. The locking member 154 may be driven by an actuator or any other device (not shown) to disengage from the platform 152 upon receiving a signal from the controller 120. When the locking member 154 is engaged with the platform 152, the platform 152 is retained in the first, lowered position which results in the drug delivery device 101 being retained within the storage compartment 112. In other words, the platform 152 is restricted from moving upwardly into the second, raised position when the locking member 154 is engaged. When the locking member 154 is disengaged from the platform 152, the platform 152 may then move to the second, raised position. In some examples, the locking member 154 may be in the form of any number of latches or fingers that directly engage a portion of the drug delivery device 101 to retain the drug delivery device 101 within the storage compartment 112. Other examples are possible.

The drive member 156 may be any component or arrangement of components capable of exerting an urging force on the platform 152 to move the platform 152 to the second, raised position. In the illustrated example, the drive member 156 is in the form of a compression spring that is operably coupled to the platform 152. In this arrangement, when the platform 152 is in the first, lowered position, the drive member 156 is in a compressed or loaded state. The force exerted by the locking member 154 on the platform 152 is greater than the force exerted by the drive member 156 on the platform 152, and as such, the platform remains in this first, lowered position. However, upon the locking member 154 disengaging from the platform 152, the force exerted by the drive member 156 then moves the platform 152 to the second, raised position. In some examples, the drive member 156 may additionally include a return mechanism (not illustrated) such as a gear, a pulley, a solenoid, or any other device that, when activated by the controller 120, causes the platform 152 to again be lowered to the first, lowered position. In other examples, the drive member 156 may be in the form of a reversible motor or actuator capable of exerting forces in opposing directions to selectively raise or lower the platform 152 upon receiving a signal from the controller 120. Other examples are possible.

The storage container 110 further includes an interface 170 having any number of components such as a display 172, input buttons 174, and the like that are configured to communicate information to and from the controller 120. In some examples, the interface 170 may additionally include any number of illumination devices, audio emitters, haptic feedback devices, and the like. Other examples are possible. The interface 170 may be disposed on or near any portion of the storage container 110 such as on any surface, on an edge of the storage container 110, and the like. The interface 170 allows a user to input any number of user inputs such as a desired drug delivery time, date, and/or recurring schedule, a dosage quantity, desired temperature set points including storage temperature ranges, administration temperature ranges, notifications such as dose reminders, a delay time at which the drug delivery device 101 will be withdrawn back into the storage container 110, expiration dates of the medicine, push notifications, and the like. In some examples, some or all of the programming features may be programmed through a secondary programming interface (e.g., a mobile device, a personal computer, a tablet, etc.) by individuals who are authorized to read and/or adjust the programming of the system 100 such as healthcare professionals and/or administrators.

The interface 170 may additionally include security features such as a password protection and/or encryption that require a user to enter a correct password prior to gaining entry to the device. In these examples, the system 100 may include an additional locking mechanism coupled to the lid 111 that prevents access to the inside of the storage container 110 unless the correct password is entered, and thereby creates an additional level of privacy and assurance that non-patients may not gain access to the drug delivery device 101. Other examples are possible.

In use, a user or healthcare provider may insert the drug delivery device or devices 101 into the storage compartment or compartments 112, and may activate the storage container 110 via the interface 170. In some examples, the storage container 110 may have a scanning system (not shown) capable of reading label information on the drug delivery device 101 and transmitting this information to the controller 120 to automatically determine an appropriate storage temperature. In any of these examples, the controller 120 sends a signal to the temperature control device 140 that causes it to cool the storage compartments 112 to the storage temperature (e.g., approximately 2° C., or in some examples, within a desired approximate temperature range). A user may then preprogram the storage container 110 (via the interface 170) to warm a drug delivery device 101 to a desired temperature on a desired date and time and/or interval (e.g., weekly on Monday mornings at 7:30 am). The controller 120 will then initiate a warming cycle that warms a particular storage compartment 112 to the desired administration temperature such that the administration temperature is obtained at the desired time. Such a system may employ a feedback loop to adjust timing and any other heating properties of the temperature control device 140.

Once the temperature in the storage compartment 112 (measured by the temperature sensor 130) reaches the desired administration temperature, the controller 120 then transmits a signal to the retention mechanism 150 that causes the locking member 154 to disengage from the platform 152. As a result, and as illustrated in FIG. 4, the drive member 156 urges the platform 152 to the second, raised position where the warmed drug delivery device 101 extends out of the storage compartment 112. The interface 170 may provide a visual, audio, and/or haptic feedback to indicate that the drug delivery device 101 is ready to be administered.

The controller 120 may then initiate a timing sequence or countdown of a predetermined time in which the drug delivery device 101 must be removed from the storage compartment 112. In some examples, this predetermined time is approximately 30 minutes, but other examples or ranges are possible. In the event that the drug delivery device 101 is not removed from the storage compartment 112 within this predetermined time, the controller 120 may then send another signal to the retention mechanism 150 that causes the platform 152 to lower to the first, lowered position (as illustrated in FIG. 3), thus re-securing the drug delivery device 101 within the storage compartment 120 and may again initiate a cooling routine that causes the temperature control device 140 to lower the temperature in the storage compartment 112 to the storage temperature, thereby preventing the drug contained in the drug delivery device 101 from spoilage. The controller 120 may transmit a signal to the interface 170 that causes the display 172 to indicate that a delivery window was missed, and may prompt the user to input a new desired administration time.

Figure 5:
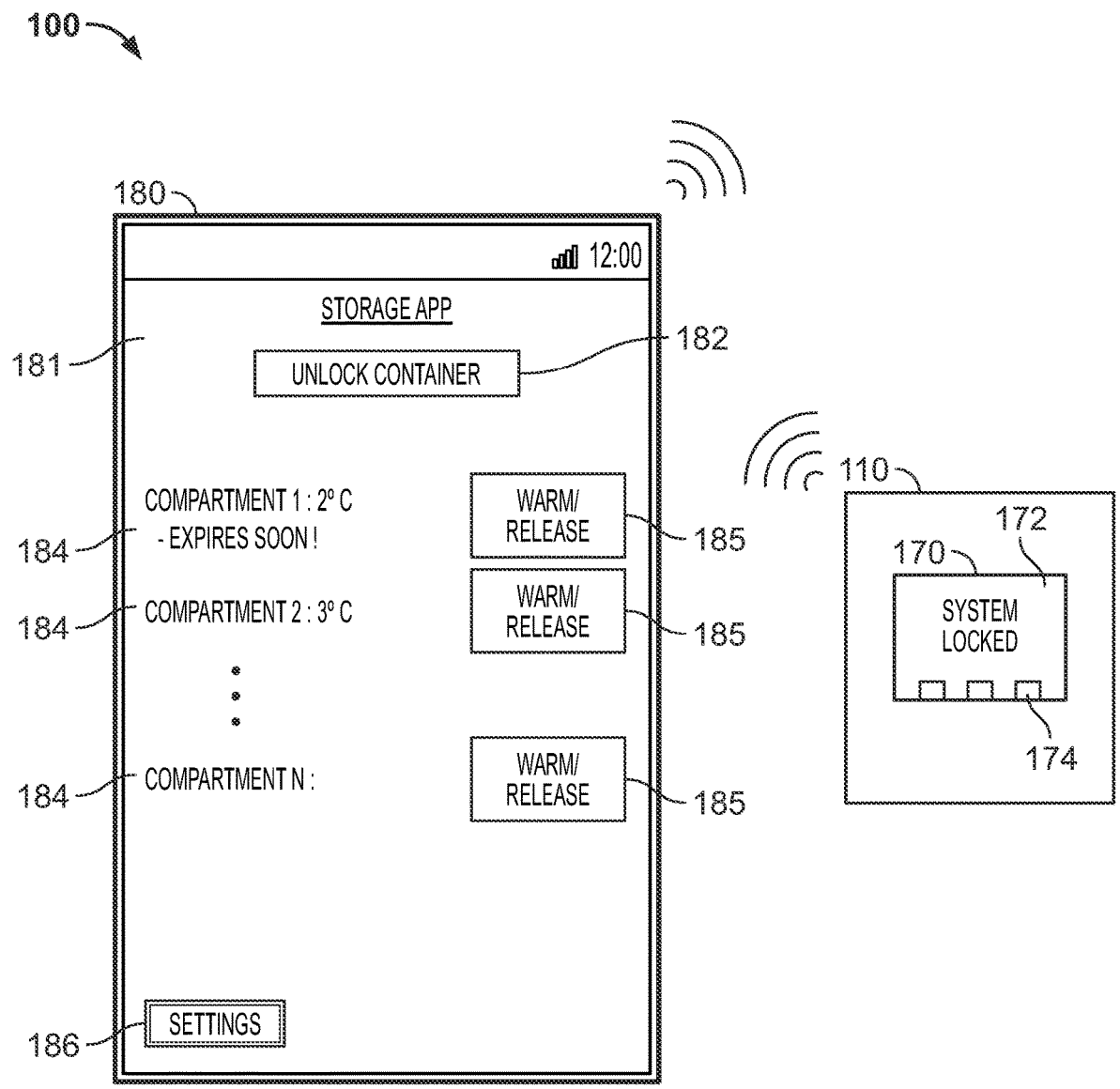
FIG. 5 illustrates a schematic view of an example personal computing device interface for communicating with the example system of FIGS. 1-4 in accordance with various embodiments.

As noted, the system 100 may incorporate advanced connectivity features such as Bluetooth, Wi-Fi, or Cellular communication protocols to provide state and function of the system 100 to a remote system such as mobile phone or other computing device or any other cloud-based service. Such a system may be capable of receiving or transmitting information. For example, the patient could use their mobile phone or other connected device to program the system 100 to immediately warm a drug delivery device 101 for administration. The controller 120 may then transmit a signal to the patient's mobile device that may arrive as a push notification which is immediately viewable by the patient, and thus may improve adherence to the prescribed therapy. For example, as illustrated in FIG. 5, a computing device 180 is provided that includes an application 181 allowing user inputs to interface with the storage container 110. The application 181 may include a selection 182 to unlock the container 110 to provide access to the storage compartments 112 or any other components retained therein. Further, the application 181 may include an indication 184 of available storage compartments 112, and may provide a visual indication of the current status (e.g., temperature, expiration, etc.). Further, the application 181 may include an input 185 to selectively warm and release a desired compartment. An additional settings input 186 may allow the user to configure any number of features such as a desired schedule, temperatures or temperature ranges, etc. Other examples are possible.

In addition, the system 100 may be programmed provide the patient with information on the number of drug delivery devices 101 remaining in the storage container 110 and may prompt the patient to reorder. Alternatively, the system 100 may be configured to automatically reorder when the number of units remaining reaches a defined amount, or by calendar period. Any number of these states and/or modes may be bi-directionally programmed or communicated. Further still, the user may be able to unlock the container 110 by transmitting a command using their personal computing device, and in some examples, the mere proximity of the personal computing device to the system 100 may be sufficient to unlock the container 110.

So configured, a small, tabletop storage system is provided that can provide for automated preparation of a users prescribed medication regimen. The system 100 may include any number of additional features to improve its functionality. For example, the system 100 may use a portable power system that is rechargeable in order to allow the user to bring the system 100 with them to other locations if needed. In these examples, the users settings will remain stored to the memory of the controller 120 even in the event of power loss.

Further, in some examples, the system 100 may track each individual storage compartment 112 to determine the appropriate storage delivery compartment 112 to use based on an expected expiration date of the drug contained within the drug delivery device 101. In some approaches, the system 100 may be designed to hold a series of carriers or cradles that are designed to hold a specific type or configuration of drug delivery devices or containers. In this embodiment, the system 100 may accommodate one or multiple cradles having the same overall design but may have specific features that are designed to house the particular device/container to be inserted. This provides the flexibility for the system to accommodate multiple different drug delivery device container combinations within a common storage container. For example, a system 100 may include eight cradles, and two of which may have internal features to hold a first type of drug delivery device, two may have internal features to hold a second type of drug delivery device, and so on. In this example, all of these devices will be housed within the storage container 110 in its respective cradle and all the features and functions described above could be utilized including the heating and ejection function. Additionally, the cradles could be coded so that the storage container 110 recognizes what type device is housed therein and the features and/or functionality of the storage container 110 may automatically be changed due to device type. The cradle may be coded via an optical identification of color, near-field communication (NFC), a bar code, Bluetooth, or any other encoding technologies. If the system 100 is designed with separate cooling and heating chambers for each of the cradles (or devices), it could be programmed for different cooling and heating temperatures for each device type and can be automatically set based on cradle coding. Accordingly, a healthcare professional may use the system 100 to store and administer a variety of medicaments in their office.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-a4β7 mAb); MLN1202 (anti-CCR2 chemokine mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker); Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-a4integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-a5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE3 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery system comprising:
   a drug delivery device adapted to deliver a medicament to a user; and
   a storage container having a container body including at least one storage compartment, the storage container including:
   a controller operably coupled to the storage container and being adapted to control operation thereof,
   at least one temperature sensor associated with the at least one storage compartment and being communicatively coupled to the controller to measure a temperature of the at least one storage compartment and transmit the measured temperature to the controller,
   at least one temperature control device associated with the at least one storage compartment, the at least one temperature control device being communicatively coupled to the controller to adjust a temperature of the at least one storage compartment, and
   at least one retention mechanism coupled to the storage container, the at least one retention mechanism being communicatively coupled to the controller to selectively retain the drug delivery device within the at least one storage compartment,
   wherein in response to a user input, the controller is adapted to:
   first, activate the at least one temperature control device to adjust the temperature in the at least one storage compartment to an administration temperature,
   second, transmit a signal to the at least one retention mechanism to release the drug delivery device from the at least one storage compartment after the temperature in the at least one storage compartment reaches the administration temperature,
   third, if the drug delivery device has not been removed from the at least one storage compartment within a predetermined time period, transmit a signal to the at least one retention mechanism to re-secure the drug delivery device within the at least one storage compartment and reactivate the at least one temperature control device to adjust the temperature in the at least one storage compartment to a storage temperature.

2. The drug delivery system of claim 1, wherein the predetermined time is approximately 30 minutes.

3. The drug delivery system of claim 1, wherein the at least one temperature control device includes at least one of a cooling element or a heating element.

4. The drug delivery system of claim 1, wherein the at least one temperature controller is adapted to adjust the temperature between a cooling temperature and the administration temperature.

5. The drug delivery system of claim 1, wherein the release mechanism comprises a locking member adapted to provide access to the at least one storage compartment.

6. The drug delivery system of claim 1, further comprising a plurality of storage compartments each being adapted to contain a drug delivery device therein, each of the plurality of storage compartments having a respective retention mechanism adapted to selectively retain the drug delivery device in the respective storage compartment.

7. The drug delivery system of claim 6, further comprising a plurality of temperature control devices, each of the plurality of temperature control devices being associated with one of the plurality of storage compartments.

8. The drug delivery system of claim 1, wherein the at least one retention mechanism comprises a movable platform that selectively raises or lowers the drug delivery device.

9. The drug delivery system of claim 1, further comprising an interface adapted to receive the user input, wherein the user input includes at least one of a desired drug delivery time, a dosage quantity, or a temperature set point.

10. An automated storage container for storing a drug delivery device, the container comprising:

at least one storage compartment dimensioned to accommodate the drug delivery device;
a controller operably coupled to the storage container and being adapted to control operation thereof;
at least one temperature sensor associated with the at least one storage compartment and being communicatively coupled to the controller to measure a temperature of the at least one storage compartment and transmit the measured temperature to the controller;
at least one temperature control device associated with the at least one storage compartment, the at least one temperature control device being communicatively coupled to the controller to adjust a temperature of the at least one storage compartment; and
at least one retention mechanism coupled to the storage container, the at least one retention mechanism being communicatively coupled to the controller to selectively retain the drug delivery device within the at least one storage compartment;
wherein in response to a user input, the controller is adapted to:
first, activate the at least one temperature control device to adjust the temperature in the at least one storage compartment to an administration temperature,
second, transmit a signal to the at least one retention mechanism to release the drug delivery device from the at least one storage compartment after the temperature in the at least one storage compartment reaches the administration temperature, and
third, if the drug delivery device has not been removed from the at least one storage compartment within a predetermined time period, transmit a signal to the at least one retention mechanism to re-secure the drug delivery device within the at least one storage compartment and reactivate the at least one temperature control device to adjust the temperature in the at least one storage compartment to a storage temperature.

11. The automated storage container of claim 10, wherein the at least one temperature control device includes at least one of a cooling element or a heating element.

12. The automated storage container of claim 10, wherein the at least one temperature controller is adapted to adjust the temperature between a cooling temperature and the use temperature.

13. The automated storage container of claim 10, wherein the at least one retention mechanism comprises a locking member adapted to provide access to the at least one storage compartment.

14. The automated storage container of claim 10, further comprising a plurality of storage compartments each being adapted to contain a drug delivery device therein, each of the plurality of storage compartments having a respective retention mechanism adapted to selectively retain the drug delivery device in the respective storage compartment.

15. The automated storage container of claim 14, further comprising a plurality of temperature control devices, each of the plurality of temperature control devices being associated with one of the plurality of storage compartments.

16. The automated storage container of claim 10, wherein the at least one retention mechanism comprises a movable platform that selectively raises or lowers the drug delivery device.

17. The automated storage container of claim 10, further comprising an interface adapted to receive the user input.

18. The automated storage container of claim 17, wherein the user input includes at least one of a desired drug delivery time, a dosage quantity, or a temperature set point.

* * * * *